United States Patent
Dusbabek et al.

(10) Patent No.: US 9,326,783 B2
(45) Date of Patent: May 3, 2016

(54) REMOVAL TOOL FOR USE WITH ENDOSCOPIC DEVICE

(71) Applicant: RSH, LLC, Houston, TX (US)

(72) Inventors: Andrew Joseph Dusbabek, Dayton, MN (US); Scott Arvin Olson, Princeton, MN (US); Christen Andrew Springs, Houston, TX (US); Isaac Raijman, Houston, TX (US)

(73) Assignee: RSH, LLC, Houston, TX (US)

( * ) Notice: Subject to any disclaimer, the term of this patent is extended or adjusted under 35 U.S.C. 154(b) by 356 days.

(21) Appl. No.: 13/843,891

(22) Filed: Mar. 15, 2013

(65) Prior Publication Data

US 2014/0277063 A1 Sep. 18, 2014

(51) Int. Cl.
*A61B 17/22* (2006.01)
*A61M 31/00* (2006.01)
*A61M 25/10* (2013.01)

(52) U.S. Cl.
CPC . *A61B 17/22032* (2013.01); *A61B 2017/22067* (2013.01); *A61B 2017/22082* (2013.01); *A61M 31/005* (2013.01); *A61M 2025/1079* (2013.01); *A61M 2025/1084* (2013.01)

(58) Field of Classification Search
CPC ............ A61B 17/22031; A61B 17/22032; A61B 2017/22067; A61B 2017/22082; A61M 2025/1079; A61M 2025/1087; A61M 2025/109; A61M 31/005; A61M 5/007
See application file for complete search history.

(56) References Cited

U.S. PATENT DOCUMENTS

| | | | | |
|---|---|---|---|---|
| 4,295,464 A * | 10/1981 | Shihata | ............ | A61B 17/22032 604/101.05 |
| 4,469,100 A * | 9/1984 | Hardwick | ........ | A61B 17/22032 604/908 |
| 4,930,496 A * | 6/1990 | Bosley, Jr. | ........ | A61B 17/22032 601/4 |
| 5,059,178 A * | 10/1991 | Ya | ........... | A61B 17/22 604/101.03 |
| 5,195,955 A * | 3/1993 | Don Michael | ... | A61B 17/12109 604/22 |
| 5,334,143 A * | 8/1994 | Carroll | .................. | A61M 29/02 604/102.02 |
| 6,056,721 A * | 5/2000 | Shulze | ............. | A61M 25/0032 600/191 |
| 6,547,760 B1 * | 4/2003 | Samson | ........... | A61B 17/12045 604/101.01 |
| 6,692,484 B1 * | 2/2004 | Karpiel | ............ | A61B 17/22031 600/31 |
| 6,695,811 B2 * | 2/2004 | Samson | ........... | A61B 17/12045 604/101.01 |
| 8,029,494 B2 * | 10/2011 | Dua | .................. | A61M 25/1006 604/509 |
| 2001/0001113 A1 * | 5/2001 | Lim | ........................ | A61F 2/958 604/96.1 |
| 2003/0036728 A1 * | 2/2003 | Samson | ........... | A61B 17/12045 604/103.01 |
| 2003/0236496 A1 * | 12/2003 | Samson | ........... | A61B 17/12036 604/103.02 |
| 2004/0267195 A1 * | 12/2004 | Currlin | .................... | A61F 2/958 604/103.1 |

(Continued)

*Primary Examiner* — Ryan J Severson
(74) *Attorney, Agent, or Firm* — Berkeley Law & Technology Group, LLP (57) ABSTRACT

Briefly, in accordance with one embodiment, a tool for use with an endoscopic procedure comprises an expandable thermoplastic polyurethane vessel. The expandable vessel may be fused to a shaft and may be configured to receive a fluid from the shaft. The shaft may comprise a distal port and a proximal port configured to dispense a dye material exterior to the expandable vessel.

18 Claims, 4 Drawing Sheets

(56) References Cited

U.S. PATENT DOCUMENTS

| | | | | |
|---|---|---|---|---|
| 2005/0228417 A1* | 10/2005 | Teitelbaum | A61B 17/22031 | 606/159 |
| 2007/0270897 A1* | 11/2007 | Skerven | A61B 1/00082 | 606/192 |
| 2008/0188866 A1* | 8/2008 | Karpiel | A61B 17/22032 | 606/127 |
| 2008/0243068 A1* | 10/2008 | Ramzipoor | A61B 17/12022 | 604/103.01 |
| 2009/0171369 A1* | 7/2009 | Gayzik | A61B 17/22032 | 606/127 |
| 2009/0187098 A1* | 7/2009 | Makower | A61B 17/12022 | 600/424 |
| 2009/0187144 A1* | 7/2009 | Jayaraman | A61M 25/1002 | 604/103.02 |
| 2009/0306769 A1* | 12/2009 | Schewe | A61M 25/1029 | 623/1.34 |
| 2013/0237950 A1* | 9/2013 | Gianotti | A61F 2/958 | 604/500 |
| 2014/0276530 A1* | 9/2014 | Gianotti | A61M 25/1002 | 604/500 |
| 2014/0276585 A1* | 9/2014 | Gianotti | A61M 25/10184 | 604/506 |
| 2014/0277063 A1* | 9/2014 | Springs | A61B 17/22031 | 606/192 |

* cited by examiner

REMOVAL TOOL FOR USE WITH ENDOSCOPIC DEVICE

CROSS-REFERENCE TO RELATED APPLICATION

Although claimed subject matter is not necessarily limited in scope in this respect, additional example embodiments of REMOVAL TOOL FOR USE WITH ENDOSCOPIC DEVICE may be discussed in concurrently filed U.S. patent application Ser. No. 13/843,982, titled MULTI-LUMEN SHAFT USED WITH ENDOSCOPIC DEVICE, by Isaac Raijman et al, herein incorporated by reference in its entirety and assigned to the assignee of currently claimed subject matter.

BACKGROUND

1. Field

This disclosure relates to devices that may be used, for example, in association with endoscopic surgery.

2. Information

At times, there may be a need to remove an object from one or more of an individual's body orifices, including orifices within the alimentary canal. To remove an object from an orifice within an individual's alimentary canal, such as a stone or other object lodged in a bile duct, endoscopic surgery may be performed. Endoscopic surgery may entail, for example, use of an endoscopic device that may be equipped with a camera that is entered into an individual's mouth and advanced through the alimentary canal until appropriately positioned within the individual's duodenum so that a stone or other object may be removed. However, endoscopic surgery may represent a time-consuming process in which an endoscope, and object removal tools, may be positioned into place by way of a working channel of an endoscope. Once in position, for example, removal of the stone or other object may involve a high degree of cooperation between the endoscope and the removal tools, for example. On occasion, cooperation among an endoscope and removal tools may be in need of improvement to bring about decreases in endoscopic surgery costs, decreases in surgeon and support staff time, as well as reducing a level of discomfort of the patient undergoing endoscopic surgery.

BRIEF DESCRIPTION OF DRAWINGS

Claimed subject matter is particularly pointed out and distinctly claimed in the concluding portion of the specification. However, both as to organization and/or method of operation, together with objects, features, and/or advantages thereof, claimed subject matter may best be understood by reference to the following detailed description if read with the accompanying drawings in which:

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

Reference throughout this specification to "one example," "one feature," "one embodiment," "an example," "a feature," "an implementation," or "an embodiment" means that a particular feature, structure, or characteristic described in connection with the feature, example, or embodiment is included in at least one feature, example, or embodiment of claimed subject matter. Thus, appearances of the phrase "in one example," "an example," "in one implementation," "an implementation," "an embodiment," or "in one embodiment" in various places throughout this specification are not necessarily all referring to the same feature, example, or embodiment. Particular features, structures, or characteristics may be combined in one or more examples, features, or embodiments. The term "patient" and "individual" may be used interchangeably herein. The terms "duct," "ostium," "opening," and "orifice," as used herein, may comprise an opening into a vessel and/or cavity of the body. It should be noted that although significant portions of the description of embodiments may be directed toward removal of a stone or other object lodged within a bile duct, embodiments are not limited to such uses, and claimed subject matter is intended to embrace various applications such as those involving other portions of the alimentary canal, other orifices and structures of a human patient, orifices and structures of an animal patient, or intricate mechanical assemblies and/or structures.

A removal tool may be used with an endoscope to assist in removing an object, such as a stone lodged in one or more of bile ducts, for example, of an individual. A stone or other object may be dislodged from a bile duct by, for example, urging the object toward an ostium or other opening which permits the object to pass through the opening and into the duodenum, for example. Responsive to entry into the duodenum, the object may be may be disposed of via normal discharge of solid waste from the body. Subsequent to entry of the object into the duodenum, the removal tool may be stowed within an endoscopic device and the endoscopic device may be withdrawn from the body through the alimentary canal, for example.

A removal tool, which may comprise an expandable vessel, such as a balloon, may be formed from a thermoplastic polyurethane material. A removal tool may be conveyed through a working channel of an endoscopic device after the endoscopic device is positioned within a body cavity. A camera located proximate with a distal end portion of an endoscopic device may be employed to provide imagery to a surgeon, for example, to inform the surgeon that a portion of an endoscopic device may be in position to deploy a removal tool. A guide wire may be extended from the endoscopic device and advanced through an ostium, such as the hepatopancreatic ampulla. A shaft coupled to the guide wire may follow the inserted guide wire through an ostium, for example, and advanced to a location nearby a stone or other object to be removed. Contrast dye, which may be visible through a radio-imaging device (i.e., x-ray machine, computer aided tomographic scanner, or the like) may be dispensed through a manifold coupled to a shaft and released under pressure to an expandable vessel and may assist a surgeon in detecting an approximate location of an object to be removed. At an appropriate time, volume of an expandable vessel may be increased through the use of a compressible and/or incompressible fluid dispensed from a shaft until the expandable vessel occupies a threshold volume. The shaft and expandable vessel may then be urged toward an ostium, in a manner that pushes the stone or other object through the ostium.

In embodiments, a thermoplastic urethane expandable vessel may be fused to a polyurethane shaft, for example, by way of a thermoplastic welding process. In embodiments, a thermoplastic welding process may give rise to fusing an expandable vessel to a cylinder-shaped polyurethane shaft at one or more locations along a periphery of the shaft. Accordingly, an expandable vessel may be unlikely to separate from a polyurethane shaft thereby enhancing ease of removal of a stone or other object from an orifice. A polyurethane shaft may comprise one or more output ports for dispensing contrast dye, which may permit a surgeon to observe areas proximate with an object to be removed, as well as observing nearby structures, such as, for example, a biliary tree that may be distal from an object to be removed. A thermoplastic urethane expandable vessel may further include a radiopaque marking, such as a radiopaque medical ink.

In an embodiment, a pair of radiopaque markings may be spaced a particular distance from one another if an expandable vessel is deflated, for example. If an expandable vessel becomes inflated, a distance between radiopaque markings may increase, thereby allowing a surgeon to assess an extent to which a vessel has been inflated. In embodiments, an expandable vessel may be exposed to an electron beam, which may sanitize a thermoplastic polyurethane expandable vessel, for example, and/or may serve to cross-link polymers in a manner that increases strength of thermoplastic polyurethane. In embodiments, an expandable vessel may be inflated using, for example, saline solution. In expandable vessel may be configured, for example, to be nonreactive with a saline solution.

Embodiments may represent a significant performance increase over conventional latex-based expandable vessels. Latex-based vessels, for example, may be prone to breakage, leakage, and/or separation from a shaft to which a latex-based vessel may be attached. In particular conventional implementations, latex-based vessels may be affixed to a shaft using an adhesive. However, in many instances, such adhesive does not possess sufficient bonding strength to resist shear and/or other stresses that may be encountered during inflation, and/or removal of objects from body orifices, for example. In response to breakage, leakage, and/or separation, a shaft and latex vessel may be removed from a patient so that another attempt at stone or other object removal may be performed. Often, removal of a shaft may involve drawing of the shaft proximately through a working channel of an endoscopic device so that a new shaft and expandable vessel can be reinserted and advanced into a patient's alimentary canal. The shaft and latex-based expandable vessel may be repositioned in an individual's alimentary canal and the object removal process may be reattempted. In many instances, this may give rise to an undesirable increase in surgeon and support staff time, an increase in equipment costs, and an increase patient discomfort.

Use of expandable vessels comprising materials other than latex may also benefit healthcare workers, such as surgeons and support staff, involved in endoscopic procedures. For example, if an endoscopic surgeon or other individual involved in endoscopic procedures suffers from an allergy to latex, the individual may employ material handling practices to reduce exposure. Further, patients who suffer from latex allergies may also experience inflammation and/or additional undesirable consequences in response to exposure to latex-based expandable vessels. Accordingly, use of thermoplastic polyurethanes, for example, may represent a means of avoiding such exposure, which may reduce undesirable consequences associated with exposure to latex-based expandable vessels, for example.

According to one illustrative embodiment, as disclosed herein, a thermoplastic polyethylene expandable vessel may be welded to a cylinder-shaped polyurethane shaft. An expandable vessel may encircle a polyurethane shaft and may be thermoplastically welded or otherwise fused to the shaft, for example. Saline solution, delivered to an expandable vessel at a suitable pressure, may inflate a vessel to a diameter of, for example, between approximately 5.0 mm and approximately 25.0 mm. It has been observed that a thermoplastic polyethylene expandable vessel of approximately 5.0 mm to approximately 25.0 mm may be of sufficient girth to form a temporary seal such that, when drawn towards the ostium, for example, stones or other objects may be urged along the biliary duct, for example, and through a patient's ampulla of vater (i.e., the hepatopancreatic ampulla) and into the patient's duodenum. Due at least in part to increased strength of expandable vessel, such object removal may be performed in a single attempt.

Figure 1:
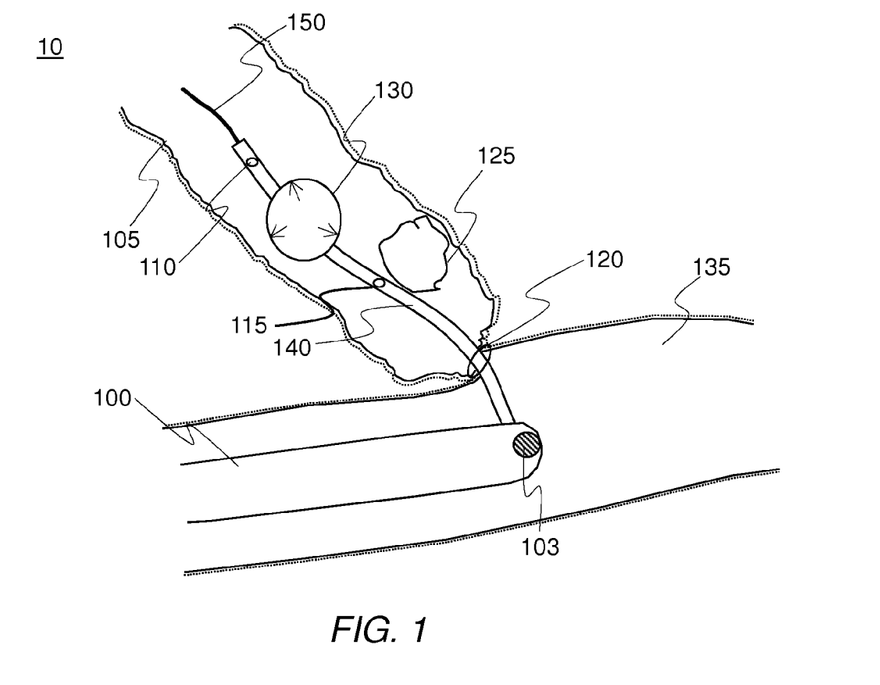
FIG. 1 is a diagram of an embodiment showing use of an endoscope and removal tool deployed in an alimentary canal.

FIG. 1 is a diagram of an embodiment 10 showing use of an endoscope and removal tool deployed in an alimentary canal. In accordance with a conventional endoscopic procedure, endoscopic device 100, for example, may be advanced through a patient's alimentary canal while a patient is, for example, under sedation. Endoscopic device 100 may be advanced into a patient's mouth, into the patient's esophagus, through the cardia, stomach, and pyloric valve, for example, and into a patient's duodenum. It should be noted that embodiment 10 represents merely a single implementation of a removal tool for use with an endoscopic procedure, and claimed subject matter is not limited to any particular embodiment, such as that of FIG. 1. For example, a removal tool may be used in association with endoscopic devices and advanced into other body cavities, including body cavities of a human patient, animal patient, or into an intricate mechanical structure, for example. Further, implementations may involve the use of other types of probing devices that may be used to view internal structures of living organisms and/or mechanical apparatuses, and claimed subject matter is not limited in this respect.

Endoscopic device 100 may include camera 103 which, for example, may provide visual feedback to assist an endoscopic surgeon in positioning an endoscopic device. Although not shown in FIG. 1, endoscopic device 100 may additionally comprise a lamp or other illumination source so as to enable lighting of body cavities, such as alimentary canal 135. Further, although not shown explicitly in FIG. 1, endoscopic device 100 may include a working channel that may permit tools, utensils, and other implements to be conveyed into, for example, a patient's alimentary canal and/or other body orifice. In the example of FIG. 1, endoscopic device 100 may be used to convey shaft 140 to a location proximate with, for example, ostium 120. In an embodiment, ostium 120 represents an opening, such as the hepatopancreatic ampulla, through which guide wire 150 may be advanced.

If endoscopic device 100 is positioned proximate with ostium 120, a surgeon may advance guide wire 150 through ostium 120. Subsequent to penetration of ostium 120, shaft 140 may also be advanced through ostium 120. In an embodiment, advancement of guide wire 150 and/or shaft 140 may be enabled, at least in part, using camera 103 to obtain visual feedback of structures within, for example, alimentary canal 135.

Upon entry to biliary duct 105, by way of ostium 120, for example, shaft 140 may be at least partially advanced toward stone 125 and further (i.e., distally) into biliary duct 105. In embodiments, for example, one or more of distal shaft port 110 and proximal shaft 115 may be used to dispense contrast dye, which may be used in conjunction with a fluoroscopic device, such as an x-ray machine, to provide imagery to an endoscopic surgeon. In one exemplary embodiment, an endoscopic surgeon may locate ostium 120 by way of camera 103, and for example, upon observing the entry of guide wire 150 and at least a distal portion of shaft 140 into ostium 120, dispense of contrast dye through, for example, distal shaft port 110. Contrast dye, which may distribute within biliary duct 105, may enable a surgeon to position shaft 140 relative to stone a 125. It should be noted, however, that some embodiments may position a shaft without assistance from a contrast dye, and claimed subject matter is not limited in this regard.

If positioned within biliary duct 105, such as, for example, shown in FIG. 1, shaft 140 may introduce saline solution into expandable vessel 130. Shaft 140 may be configured to be nonreactive with saline or other solution introduced into expandable vessel 130. Under an appropriate fluid pressure, expandable vessel 130 may expand in size until, for example, vessel 130 comes into contact with an inner surface of biliary duct 105. Consequently, at least in some embodiments, expandable vessel 130 may form a temporary seal that may preclude contrast dye emanating from distal shaft port 110 to seep or leak towards ostium 120. Thus, contrast fluid may be permitted to fill biliary duct 105. Filling of biliary 105 with contrast dye may, for example, enable an endoscopic surgeon, radiologist, or other healthcare professional, for example, to observe more distal structures that may lie within and/or be in fluid communication with biliary duct 105. Thus, additional structures such as the common bile duct, pancreatic duct, cystic duct, common hepatic duct, as well as other structures may be visible if expandable vessel is permitted to form a temporary seal of at least a portion of biliary duct 105. It should be noted, however, that liquids, such as contrast dye, emanating from distal shaft port 110 may provide other benefits, and claimed subject matter is not limited in this respect.

As shown in FIG. 1, shaft 140 may additionally comprise proximal shaft port 115. In embodiments, proximal shaft port 115 may additionally be employed to distribute contrast dye within biliary duct 105, for example. Consequently, if permitted to at least partially surround stone 125, contrast dye may enable an endoscopic surgeon, radiologist, and/or other professional to monitor movement of stone 125, as expandable vessel 130 is retracted toward ostium 120. In some instances, it may be possible, for example, to observe the passing of stone 125 through ostium 120, and into alimentary canal 135. Again, however, use of contrast dye dispensed by way of distal shaft port 110 and/or proximal shaft port 115 represents one or more particular embodiments, and claimed subject matter is not limited in this respect. After stone 125 has emptied into alimentary canal 135, for example, expandable vessel 130 may be decreased in size, for example, by way of drawing saline solution from the expandable vessel, and retracting shaft 140 to a location within endoscopic device 100. Stowage of shaft 140 within endoscopic device 100 may permit an endoscopic surgeon, for example, to remove the shaft and expandable vessel device from a patient.

Figure 2A:
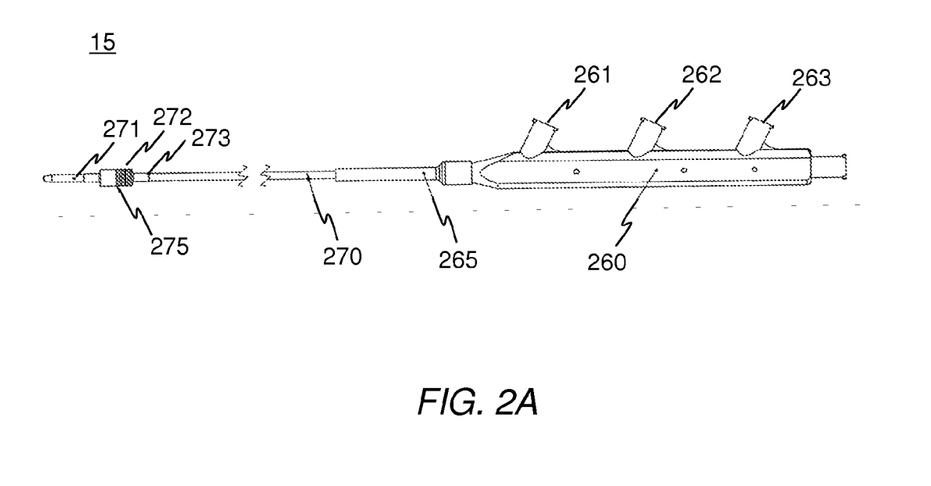
FIGS. 2A and 2B are diagrams of embodiments of a removal tool.

FIG. 2A is a diagram of an embodiment of a removal tool 15. Removal tool 15 may comprise, for example, polycarbonate manifold 260, polyolefin strain relief sheath 265, polyurethane shaft 270, and polyurethane expandable vessel 275. In embodiments, polyolefin strain relief sheath 265 may surround a portion of shaft 270 in a manner that prevents, or at least reduces likelihood of improperly bending or kinking shaft 270 as shaft 270 and expandable vessel 275 are passed through a working channel of an endoscopic device, such as endoscopic device 100. In embodiments, shaft 270 comprises a material that is nonreactive with radioimaging contrast dyes, saline solution, and/or other compressible or incompressible fluids that may be transported through manifold 260 and shaft 274 dispensing at a distal end portion of shaft 270, such as a location nearby expandable vessel 275, for example.

Manifold 260 may comprise a polycarbonate material and one or more fluid coupling ports such as fluid coupling ports 261, 262, and 263, for example. In an embodiment, fluid coupling port 261 may be used to inject radioimaging contrast dye to a distal portion of shaft 270, such as, for example, distal output port 271. Likewise, fluid coupling port 262 may be used to inject saline solution or other fluid, under suitable pressure, to inflate expandable vessel 275 through medial output port 272 (which may be obscured from view by expandable vessel 275). Likewise, fluid coupling port 263 may be used to inject radioimaging contrast dye to a proximal output port, such as, for example, proximal output port 273.

Figure 2B:
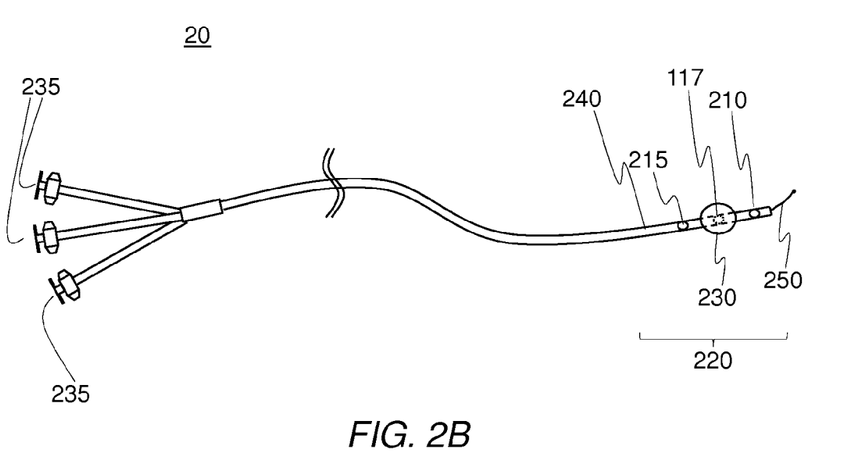

FIG. 2B is a diagram of an embodiment of a removal tool 20. The removal tool of FIG. 2B may be suitable, for example, for insertion into a working channel of an endoscopic device, such as endoscopic device 100 of FIG. 1. However, embodiment 20 may be suitable for insertion into other devices, and claimed subject matter is not limited in this respect. In embodiments, insertion into a working channel begins, for example, with insertion of distal end portion 220. If situated within an endoscopic device, removal tool 20 may be deployed, perhaps with the assistance of a camera, such as camera 103 of FIG. 1, to a location proximate with an ostium or other opening into a body cavity. Beginning with guide wire 250, shaft 240 may be inserted into an ostium.

If distal end portion 220 is positioned proximate with a stone or other object designated for removal, for example, medial shaft port 117 may dispense fluid, such as saline solution, which may increase volume of expandable vessel 230. Control for dispensing of saline solution may, for example, be provided by one or more of injector controls 235. As discussed with reference to FIG. 1, an expandable vessel may expand to form a temporary seal within a biliary duct or other structure. If at least a partial temporary seal can be formed, by way of expansion of expandable vessel 230 coming into contact an inner surface of a biliary duct, for example, contrast dye may be dispensed from one or more of distal shaft port 210 and proximal shaft port 215. Dispensing of contrast dye from distal shaft port 210 may, for example, enable an endoscopic surgeon, radiologist, or other healthcare professional to observe imagery corresponding to additional structures positioned distally from shaft 240, for example. Dispensing of contrast dye may also permit real-time observation, by way of a fluoroscope (i.e., x-ray machine) of withdrawal of shaft 240 as well as urging of a stone or other object toward a patient's alimentary canal using expandable vessel 230, for example.

Figure 3:
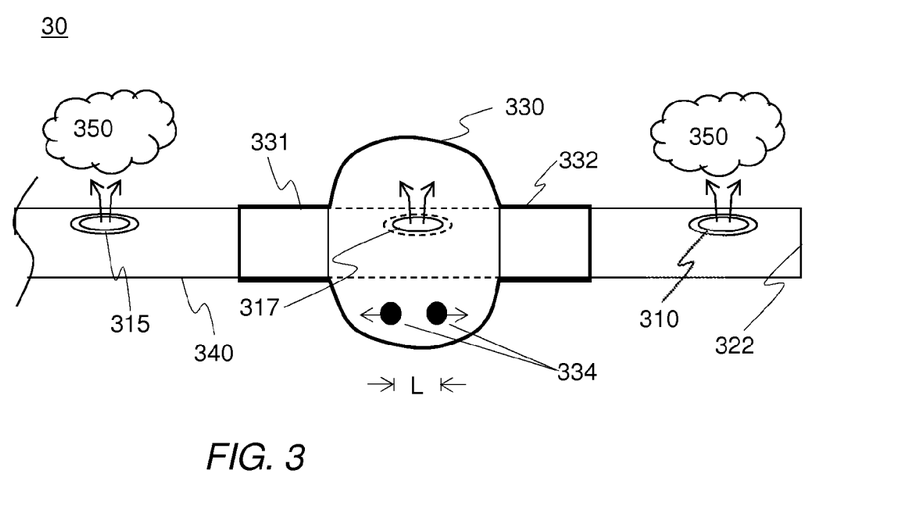
FIG. 3 is a diagram showing deployment of an embodiment of a removal tool.

FIG. 3 is a diagram showing deployment of an embodiment of a removal tool 30. In FIG. 3, shaft 340 may be advanced by guiding the shaft to follow a guide wire (not shown in FIG. 3) coupled to sealed distal end 322. Shaft 340 may be inserted into a working channel of an endoscopic device, such as endoscopic device 100 of FIG. 1, and inserted into a patient's alimentary canal, for example. After entry into a body orifice, such as an ostium (e.g., the hepatopancreatic ampulla), contrast dye 350 may be dispensed from one or more of distal shaft port 310 and proximal shaft port 315. Contrast dye may, at least in some embodiments, be employed to enable an endoscopic surgeon operating a fluoroscope to appropriately position shaft 340 proximate with a stone or other object for removal. However, removal tool 30 of FIG. 3 may be useful in a variety of other scenarios, such as object removal at other locations of a patient, and may make possible object removal from other living organisms and/or mechanical structures. Claimed subject matter is intended to embrace all such uses of removal tool 30.

At an appropriate time, saline solution may be dispensed into expandable vessel 330 way of medial shaft port 317. If dispensed at a suitable pressure, expandable vessel 330 may gain in volume until expandable vessel occupies at least a considerable cross-section of a body orifice. In FIG. 3, radiopaque markings 334, which may comprise an x-ray absorbing material, such as barium sulfate, may be observed to separate from one another as expandable vessel 330 increases in volume, for example. In other embodiments, radiopaque markings may comprise a single mark that increases in surface area as expandable vessel 330 increases in volume. In other embodiments, additional radiopaque markings may be used and may be disposed at various locations on a surface of, for example, expandable vessel 330 without limitation, and claimed subject matter is intended to embrace all such uses of radiopaque markings applied to expandable vessels. Expandable vessel 330 may be fused by way of thermoplastic welding to shaft 340 at, for example, fused portions 331 and 332. In embodiments, use of thermoplastic polyurethane expandable vessels fused to polyurethane shafts, for example, may remove a need for adhesive used for affixing expandable vessels of other compositions to shafts, such as shaft 340. In addition, use of thermoplastic polyurethane expandable vessels fused to polyurethane shafts may result, at least in part, in a much stronger bond than would result if latex expandable vessels were to be affixed, via an adhesive, to polyurethane shafts.

Figure 4:
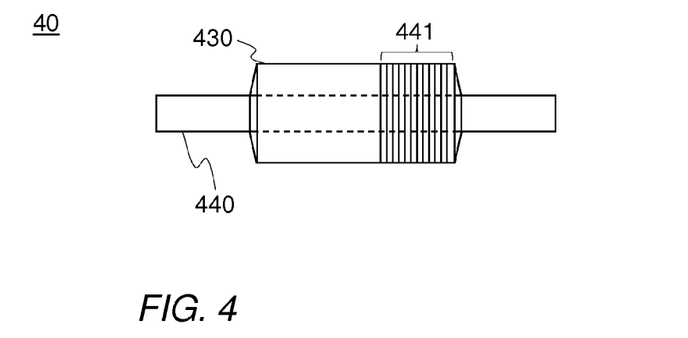
FIG. 4 is a diagram showing a portion of an embodiment of a removal tool.

FIG. 4 is a diagram showing a portion 40 of an embodiment of a removal tool. In FIG. 4, expandable vessel 430 may comprise a thermoplastic polyurethane elastomer that may be partially or fully thermoplastic. In embodiments, expandable vessel 430 may comprise a linear segment block copolymer comprising "hard" and "soft" segments. A hard segment may comprise an aromatic or aliphatic material. Aromatic thermoplastic polyurethanes may be based on isocyanates such as methylene diphenyl diisocyanate and/or related compounds. Aliphatic thermoplastic polyurethanes may be based on isocyanates such as methylene dicyclohexyl diisocyanate (H12MDI). Isocyanates may be combined with short-chain diols to form a "hard" segment. It should be noted that these are merely examples of engineered thermoplastic polyurethanes that may be used to form expandable vessel 430, however claimed subject matter is not limited in this regard.

In FIG. 4, cross-linked region 441 may indicate a portion of expandable vessel 430 that comprises additional cross-linked polymers by way of exposure to an electron beam. In embodiments, exposure to an electron beam may give rise to cross-linking of adjacent or nearby polymer chains with one another, for example. Such electron beam exposure of a portion of expandable vessel 430 may further increase strength properties of a thermoplastic polyurethane material used to form expandable vessel 430. Expandable vessel 430 may be fused to shaft 440 by way of, for example, thermoplastic welding.

Figure 5:
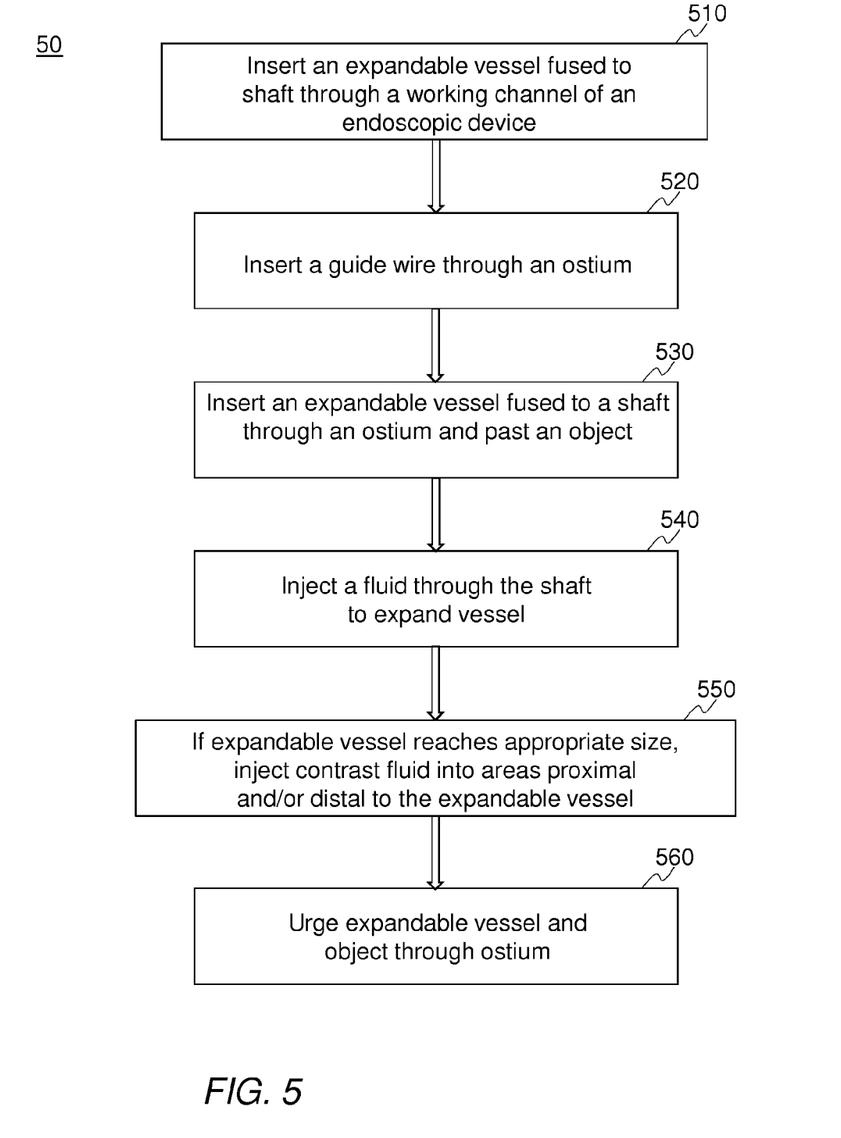
FIG. 5 is a flow diagram of a process for using an embodiment of a removal tool.

FIG. 5 is a flow diagram of a process for using an embodiment 50 of a removal tool. The arrangement of components in FIG. 1 may be suitable for performing the method of embodiment 50. However, claimed subject matter is not limited to the particular implementation of any particular figure shown and described herein and alternate arrangements of components in other implementations may be used. Example embodiments, such as embodiment 50 shown in FIG. 5 may include blocks in addition to those shown and described, fewer blocks, blocks occurring in an order different than may be identified, or any combination thereof.

At 510, an expandable vessel fused to a shaft may be inserted through a working channel of an endoscopic device. An expandable vessel may comprise a thermoplastic polyurethane material fused to a polyurethane shaft, for example, and claimed subject matter is not limited in this respect. Additionally, although expandable vessel may be inserted through an endoscopic device, expandable vessels may be inserted using other instruments, such as sigmoidoscopy devices, colonoscopy devices, or other imaging instruments, and claimed subject matter is not limited in this respect.

At 520, a guide wire may be extended from an endoscopic device and inserted through an ostium. A camera or other imaging device may be used by an endoscopic surgeon, for example, to position an endoscopic device adjacent an ostium or other structure. At 530, a shaft may be advanced through an ostium, wherein a shaft may be fused to a thermoplastic polyurethane expandable vessel, for example. 530 may also comprise dispensing a fluoroscopic contrast dye from one or more ports of a shaft so as to assist in radio imaging, for example, of an area adjacent an object lodged, such as an area immediately distal of hepatopancreatic ampulla within a patient's alimentary canal.

At 540, a fluid may be injected through a shaft to inflate an expandable vessel. For example, a saline solution may be employed to inflate or expand an expandable vessel, however, claimed subject matter is not limited to use of saline solution. In other embodiments, a variety of alternate, chemically inert compositions may be employed. At 550, if an expandable vessel reaches an appropriate size, a contrast fluid may be injected into areas proximal and/or distal to the expandable vessel. At 550, an expandable vessel of an appropriate size may assist in forming a temporary seal which may allow additional contrast dye to be ejected into a body orifice. In embodiments, this may allow imaging of additional portions of a patient's biliary tree, such as, for example, the common bile duct, the pancreatic duct, the cystic duct, the common hepatic duct, etc.

At 560, an expandable vessel and an object may be drawn (i.e. pulled) through an ostium, for example. 560 may comprise, for example, radio imaging of an area at least partially surrounding a stone or other object to be removed as the object is urged, by way of contact with an expandable vessel, towards an ostium, for example. The method may conclude with the deposit of an object to be removed into the alimentary canal where natural solid waste removal processes may take place.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to teachings of claimed subject matter without departing from one or more central concept(s) described herein. Therefore, it is intended that claimed subject matter not be limited to particular examples disclosed, but that claimed subject matter may also include all aspects falling within appended claims and/or equivalents thereof.

What is claimed is:

1. An apparatus to remove a stone from a bile duct, comprising:
a single expandable vessel fused to a shaft, the single expandable vessel to receive a compressible or incompressible fluid from a medial port of the shaft, the single expandable vessel comprising a thermoplastic polyurethane material expandable from a diameter of at least approximately 5.0 mm up to a diameter of approximately 25.0 mm, the shaft comprising a distal port and a proximal port, the distal and the proximal ports to dispense a dye material exterior to the single expandable vessel, the shaft further comprising a sealed distal end, separate from the distal port, coupled to a guide wire.

2. The apparatus of claim 1, wherein at least a portion of the single expandable vessel comprises a cross-linked thermoplastic polyurethane material.

3. The apparatus of claim 1, wherein the single expandable vessel comprises at least one radiopaque marking.

4. The apparatus of claim 3, wherein the at least one radiopaque marking comprises at least two discrete marks that separate as a volume of the single expandable vessel increases.

5. The apparatus of claim 1, wherein a portion of the shaft is surrounded by the single expandable vessel corresponding to a portion along a length of the shaft.

6. The apparatus of claim 1, wherein the single expandable vessel is to receive a saline solution from the shaft to result, at least in part, in the single expandable vessel expanding in volume.

7. The apparatus of claim 1, wherein the single expandable vessel is fused to the shaft resulting, at least in part, from a thermoplastic welding process.

8. A method of removing a stone from a bile duct, comprising:
inserting a single expandable vessel fused to a shaft through an ostium, the single expandable vessel comprising a thermoplastic polyurethane material expandable from a diameter of at least approximately 5.0 mm up to a diameter of approximately 25.0 mm; and
dispensing a contrast fluid, through distal and proximal ports exterior to the single expandable vessel, into the ostium, the distal and proximal ports being separate from a sealed distal end coupled to a guide wire.

9. The method of claim 8, and further comprising:
injecting a fluid through the shaft into the single expandable vessel.

10. The method of claim 9, and further comprising:
injecting the contrast fluid to areas proximal and/or distal to the single expandable vessel if the single expandable vessel approaches a threshold volume resulting, at least in part, from the injecting the fluid through the shaft into the single expandable vessel.

11. The method of claim 10, wherein the injecting the fluid results, at least in part, in the single expandable vessel forming a temporary seal between the single expandable vessel and an inner surface of the bile duct.

12. The method of claim 9, and further comprising:
urging the single expandable vessel towards the ostium until the stone passes the ostium.

13. The method of claim 8, and further comprising:
inserting the single expandable vessel fused to the shaft through a working channel of an endoscopic device.

14. A system for use with an endoscopic device to remove a stone from a bile duct, comprising:
a shaft, wherein a portion of the shaft is surrounded by a single vessel comprising a polyurethane expandable material;
one or more dispensing ports for injecting a compressible or incompressible fluid to result, at least in part, in an expansion of the single vessel comprising a polyurethane expandable material expandable from a diameter of at least approximately 5.0 mm up to a diameter of approximately 25.0 mm;
one or more ports proximal to the single vessel comprising a polyurethane expandable material and one or more ports distal to the single vessel comprising a polyurethane expandable material port to dispense a dye material exterior to the volume enclosed by the single vessel comprising a polyurethane expandable material; and
a sealed end, separate from the one or more proximal ports, the one or more distal ports, and the one or more dispensing ports coupled to a guide wire.

15. The system for use with an endoscopic device of claim 14, wherein at least a portion of the single vessel comprising a polyurethane expandable material comprises a cross-linked material.

16. The system for use with an endoscopic device of claim 15, wherein the one or more proximal port and the one or more distal port to dispense a fluoroscopic contrast dye.

17. The system for use with an endoscopic device of claim 14, wherein the compressible or incompressible fluid conveyed by the shaft comprises a saline solution.

18. The system for use with an endoscopic device of claim 14, wherein the shaft comprises a polyurethane material, and wherein the single vessel comprising a polyurethane expandable material is fused to the polyurethane material of the shaft.

* * * * *